United States Patent [19]
Silver

[11] Patent Number: 5,601,531
[45] Date of Patent: Feb. 11, 1997

[54] BREAST PUMP ASSEMBLY AND METHOD OF USING SAME

[75] Inventor: Brian H. Silver, Cary, Ill.

[73] Assignee: Medela, Incorporated, McHenry, Ill.

[21] Appl. No.: 390,859

[22] Filed: Feb. 16, 1995

[51] Int. Cl.$^6$ ........................................................ A61M 1/06
[52] U.S. Cl. ............................................ 604/74; 604/152
[58] Field of Search ................................ 604/74–76, 120, 604/154, 346, 119–121, 151, 152

[56] References Cited

U.S. PATENT DOCUMENTS

| | | | |
|---|---|---|---|
| D. 230,653 | 3/1974 | Zimmerman | D83/1 F |
| D. 252,470 | 7/1979 | Pawlak | D24/54 |
| D. 259,278 | 5/1981 | McCaw et al. | D24/53 |
| D. 268,871 | 5/1983 | Benham et al. | D24/53 |
| D. 282,962 | 3/1986 | Gerber | D23/43 |
| D. 307,795 | 5/1990 | Frantz | D24/17 |
| D. 314,050 | 1/1991 | Sone | D24/53 |
| 1,509,226 | 9/1924 | Brown . | |
| 1,644,257 | 10/1927 | Lasker . | |
| 1,966,498 | 7/1934 | Gross | 103/227 |
| 2,222,811 | 11/1940 | Dinesen | 230/190 |
| 2,292,527 | 8/1942 | Kraft | 60/62.6 |
| 2,419,795 | 4/1947 | Saunders | 128/297 |
| 4,067,332 | 1/1978 | O'Leary | 128/214 |
| 4,583,970 | 4/1986 | Kirchner | 604/74 |
| 4,759,747 | 7/1988 | Aida et al. | 604/74 |
| 4,857,051 | 8/1989 | Larsson | 604/74 |
| 4,929,229 | 5/1990 | Larsson | 604/74 |
| 5,007,899 | 4/1991 | Larsson | 604/74 |
| 5,287,851 | 2/1994 | Beran et al. | 128/204.23 |
| 5,295,957 | 3/1994 | Aida et al. | 604/74 |

FOREIGN PATENT DOCUMENTS

| | | | |
|---|---|---|---|
| 529424 | 7/1931 | Germany . | |
| 58990 | 12/1989 | Japan . | |
| 251810 | 9/1948 | Switzerland . | |
| 270694 | 12/1950 | Switzerland . | |
| 185521 | 9/1922 | United Kingdom . | |
| 271857 | 11/1927 | United Kingdom . | |
| 762701 | 5/1956 | United Kingdom | 81/2 |

OTHER PUBLICATIONS

Quick Disconnect Couplings, excerpt from Cole–Parmer Instrument Co. Catalog 1995–1996, pp. 413–414.

Medela Hospital Catalogue showing prior art devices, pp. 20, 21, 23–25.

*Primary Examiner*—Randall L. Green
*Assistant Examiner*—A. T. Nguyen
*Attorney, Agent, or Firm*—Brinks Hofer Gilson & Lione

[57] ABSTRACT

An improved breast pump assembly allows two breast pumps to be connected to a motor drive unit for simultaneous breast pumping. In a preferred embodiment, the improved breast pump assembly can be adjusted for either single breast pumping or for double breast pumping, depending on the particular woman's needs.

14 Claims, 5 Drawing Sheets

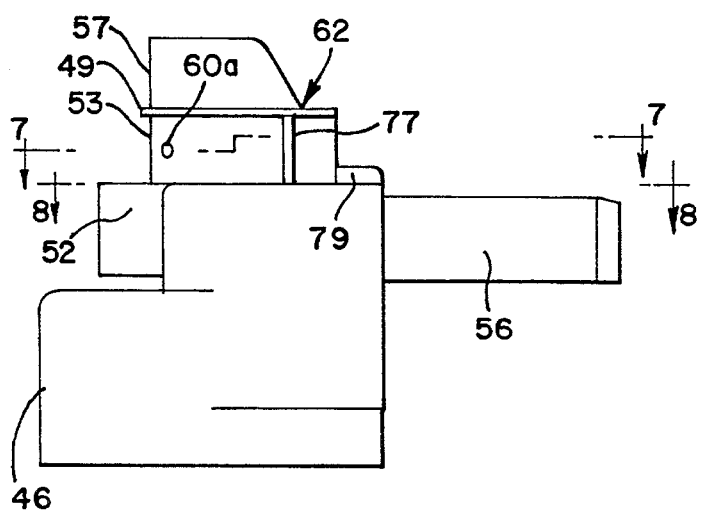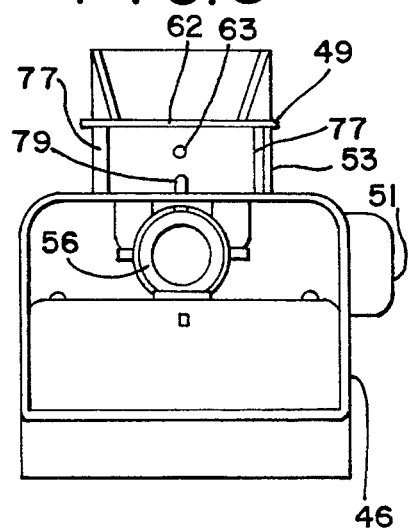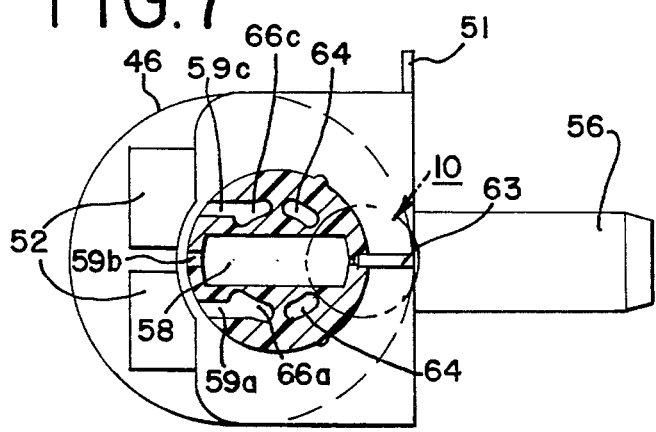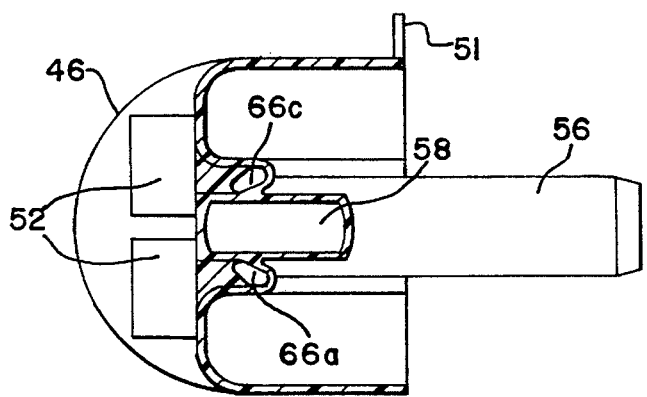

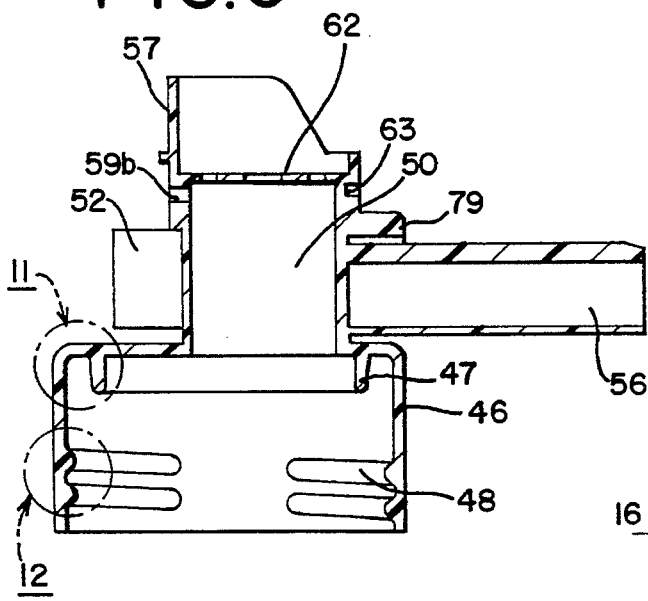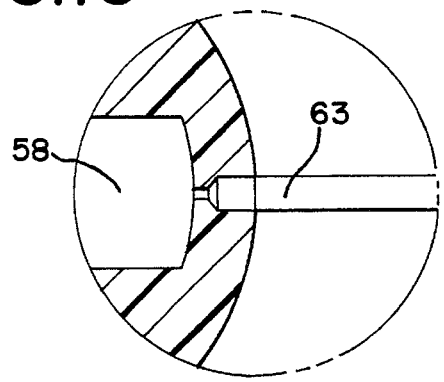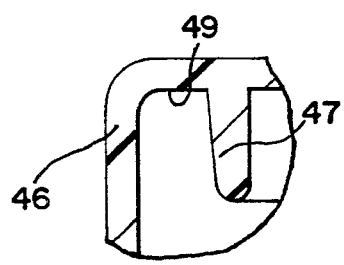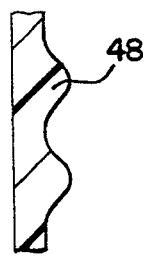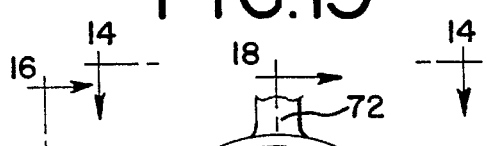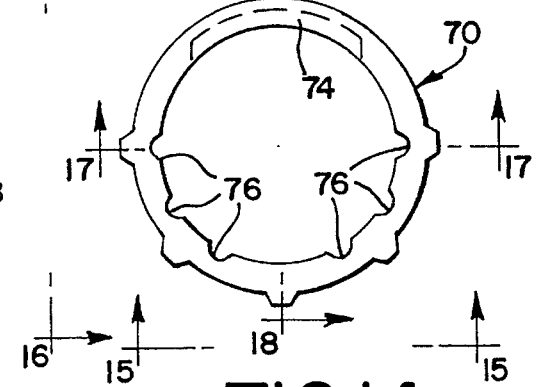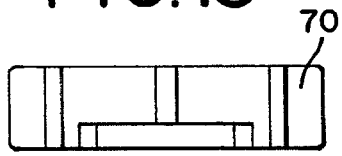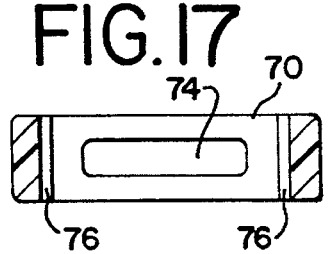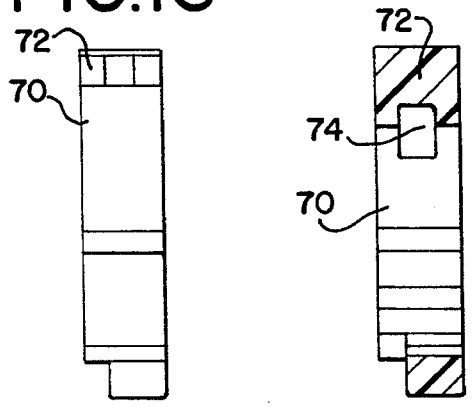

ated selector for connecting the vacuum generated by the piston pump to either or both of the breast pumps for single or double breast pumping. This enables quick and easy selection of one or both breast pumps by a simple single hand manipulation of the selector, leaving a hand free. It also enables shifting from one breast pump to the other by simply moving the selector.

BREAST PUMP ASSEMBLY AND METHOD OF USING SAME

BACKGROUND OF THE INVENTION

The present invention is directed generally to breastmilk pumps and, more particularly, to an improved breast pump assembly for expressing mothers' milk, which may be used in a manually-driven mode as well as a motor-driven mode.

Breast pumps for extracting or expressing breastmilk from a woman's breasts for later use by an infant have been available for years. Typically, these breast pumps include a funnel-shaped hood, or shield, that is placed over the nipple and a substantial portion of the breast. A reduced pressure or vacuum is intermittently generated in the hood in a manner which causes milk to be expressed from the breast within the hood. The milk then typically flows from the hood to a storage container for later use.

Generally, two types of breast pumps have been marketed for use by nursing women: motor-driven pumps; and manually-operated pumps. In manually-operated breast pumps, the intermittent suction action is typically generated by means of a compressible bulb or, more frequently, a piston-type pump. The piston pump generally includes a piston cylinder connected to the hood, and a piston slidably disposed within the piston cylinder and which is reciprocated by a hand-drivable piston rod. Motor-driven pumps typically either have a separate vacuum pump attached to the hood by tubing, or the motor is built into the hood assembly itself.

U.S. Pat. No. 5,007,899 discloses a drive unit to which the piston pump of an otherwise manually-operated breast pump can be attached for motorized breast pumping. The present invention is the particular result of improvements to the breast pump assembly disclosed in U.S. Pat. No. 5,007,899, and to the LACTINA breast pump assembly manufactured and sold by Medela, Inc. to which the foregoing patent relates.

SUMMARY OF THE INVENTION

The present invention provides an improved breast pump assembly which enables easy and effective vacuum connection of one or two breast hoods, or shields, to a piston pump, particularly where the piston pump is mounted to be driven by a motor drive unit. In a preferred embodiment of the present invention, the improved breast pump assembly can be readily adjusted through use of a selector element for either single breast pumping or for double breast pumping, depending on the particular woman's needs.

According to a first aspect of the present invention, the improved breast pump assembly includes at least one and preferably two breast pumps (i.e., shield, bottle, valving) each having a breast shield connected to an adapter device which is attached to a piston pump. The breast shields are each connected to the adapter by means of an airline (tube) between the shield and the adapter. Each of the tubes includes a male connector at one end for insertion into a mating female receptacle formed in the adapter. The Connector design provides for easy manipulation of the tube end to assure a good connection. The piston pump is preferably connected via the adapter (here, a piston cylinder holder) to a motor drive unit for reciprocating movement, but it will be seen that the inventive adapter is useful even in a manual mode of operation of the piston pump.

The present invention further provides an improved adapter for the piston pump. In a preferred embodiment of the invention, the adapter is provided with an easily-ma- These and other features and advantages of the present invention will be further understood upon consideration of the following detailed description of the present invention, taken in conjunction with the accompanying drawings, in which:

BRIEF DESCRIPTION OF THE DRAWINGS

FIG. 5 is a top view of the cylinder holder taken along line 5—5 of FIG. 2;

FIG. 6 is an elevational view of the cylinder holder taken along line 6—6 of FIG. 3;

FIG. 7 is a cross-sectional view taken along line 7—7 of FIG. 5;

FIG. 8 is a cross-sectional view taken along line 8—8 of FIG. 5;

FIG. 9 is a cross-sectional view taken along line 9—9 of FIG. 3;

FIG. 10 is an enlarged view of detail 10 shown in FIG. 7;

FIG. 11 is an enlarged view of detail 11 shown in FIG. 9;

FIG. 12 is an enlarged view of detail 12 shown in FIG. 9;

FIG. 13 is a plan view of a selector ring used with the cylinder holder shown in FIGS. 1–12 and 19–21;

FIG. 14 is a view of the selector ring taken along line 14—14 of FIG. 13;

FIG. 15 is a view of the selector ring taken along line 15—15 of FIG. 13;

FIG. 16 is a view of the selector ring taken along line 16—16 of FIG. 13;

FIG. 17 is a cross-sectional view taken along line 17—17 of FIG. 13;

FIG. 18 is a cross-sectional view taken along line 18—18 of FIG. 13;

DETAILED DESCRIPTION OF A PRESENTLY PREFERRED EMBODIMENT

A. General Organization of Elements

Figure 1:
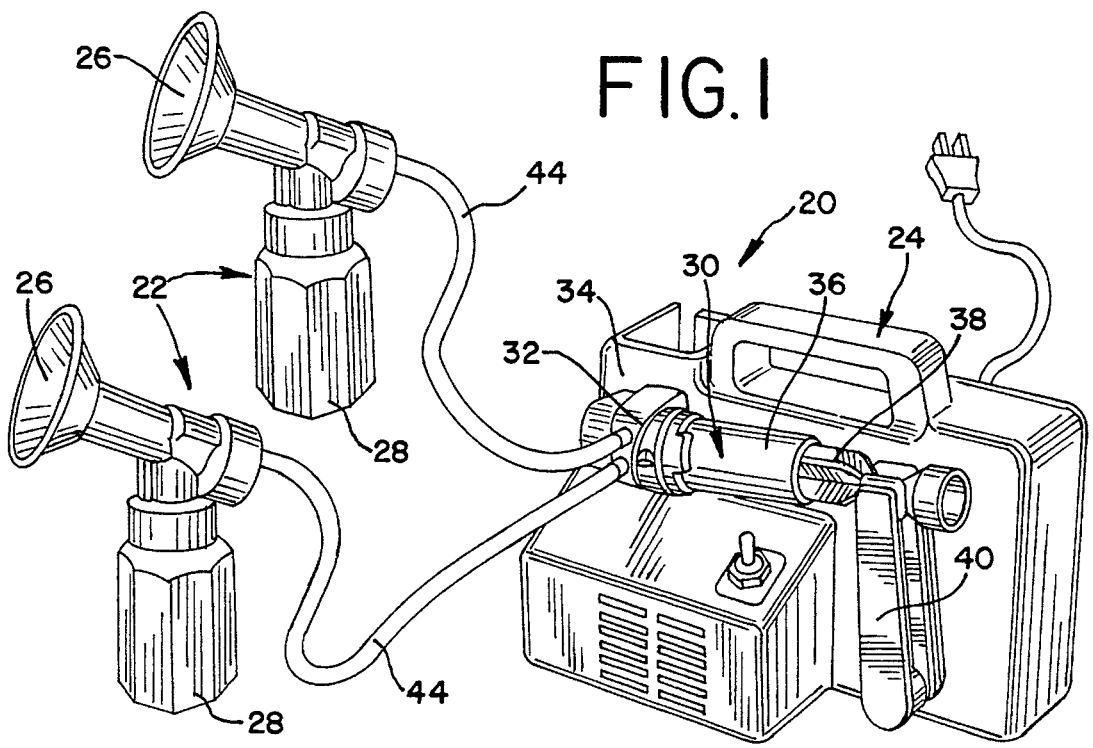
FIG. 1 is a perspective view showing a preferred embodiment of an improved breast pump assembly of the present invention.

As shown in FIG. 1, this embodiment of the improved breast pump assembly 20 of the present invention includes two breast pump units 22 and a motor drive unit 24. The breast pump units 22 have a hood assembly 26, and a container 28, such as a bottle, for collecting and storing the breast milk, which is connected to the lower portion of the hood assembly 26. The breast pumps 22 are adapted to be used with a piston pump 30. The piston cylinder of the piston pump 30 is connectable to the breast hood assembly 26 to operate the breast pump 22 in a manually-driven mode (i.e., the piston pump is reciprocated by hand). Details of this type of breast pump and the piston pump can be gleaned from U.S. Pat. Nos. 4,929,229 and 4,857,051.

The motor drive unit 24 is adapated to receive and hold the piston pump 30 of one of the breast pumps 22 when it is removed therefrom, and to mechanically drive the piston pump 30. The motor drive unit 24 is substantially as shown and described in U.S. Pat. No. 5,007,899, the disclosure of which is hereby incorporated by reference. An improved adapter or cylinder holder 32 is attachable to the casing 34 of the motor drive unit 24, and is a subject of the present application.

The piston cylinder 36 of the piston pump 30 is received in the cylinder holder 32, and the piston rod 38 is releasably held at one end of an arm 40. Arm 40 is mounted at its other end to the casing 34 to a drive system for reciprocal movement of the piston rod 38. As will be described in detail below, the cylinder holder 32 includes two ports 42 (see FIG. 2) for variously connecting the vacuum tubes 44 to the hood assemblies 26 of the respective breast pumps 22.

In brief, the motor drive 24 reciprocally moves the piston rod 38 in piston cylinder 36. The rearward stroke of the piston rod 38 generates a vacuum (negative pressure) transmitted through the cylinder holder 32 and the tubes 44 to one or both of the breast pumps 22.

B. The Adapter/Cylinder Holder

Turning once again to the drawings, FIGS. 2–21 depict various views of a preferred embodiment of the cylinder holder 32 of the present invention. As perhaps best shown in FIGS. 2–9, the improved cylinder holder 32 includes a cap portion 46 which is match-threaded at 48 for substantially airtight attachment to the forward end of piston cylinder 36. FIGS. 4, 9, 11 and 19 show that the inside of the cap portion 46 has a seal ring 47 disposed therearound for sealing engagement with the inner edge of piston cylinder 36.

Inside of the cap portion 46 is a vacuum chamber 58 that communicates with the piston cylinder 36 and, through the ports 42, with the breast pumps 22. The ports 42 are surrounded by non-circular female receptacles 52 (e.g., see FIG. 2), which are sized and shaped to snugly receive the mating male connectors 54 attached to the ends of the vacuum tubes 44, as described below and shown in FIGS. 22–27. Further, the cylinder holder 32 includes a hollow post 56 which is received within a post hole (not shown) in the casing 34 to mount the cylinder holder 32 to the motor drive unit 24. A flange 51 is formed on the exterior sidewall of the cap portion 46. The flange 51 slides into an enlarged slot (also not shown) when the post 56 is inserted in the post-hole and the cylinder holder 32 rotated into place (in a similar manner as described in U.S. Pat. No. 5,007,899). Other means for mounting the cylinder holder to the casing can be readily employed, of course.

Figure 2:
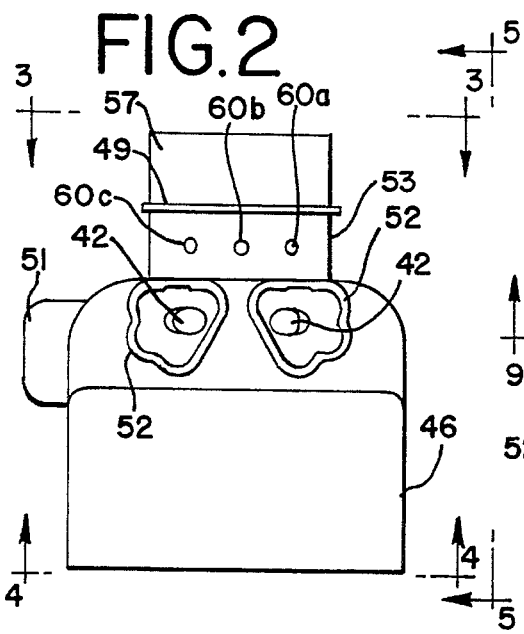
FIG. 2 is a side elevational view of the improved adapter, or cylinder holder, shown in FIG. 1, with the selector ring removed.

As shown in FIG. 2, the vacuum chamber 58 communicates with three holes 60a, 60b and 60c disposed within a collar portion 53 formed on the forward extension of cylinder holder 32. These holes are the outlets for internal passages 59a, 59b and 59c, respectively. As shown in FIGS. 7, 9 and 19–21, and as will be described in further detail hereinafter, the vacuum generated within the piston cylinder 36 is directed through the vacuum chamber 58, then through passage 59b to one or both of the passages 59a, 59c and ultimately to respective ports 42. Also, and again as described in more detail below, and as best shown in FIGS. 7 and 10, the vacuum chamber 58 includes a leakage hole 63 that connects the vacuum chamber to atmosphere in single-pumping modes of operation. This serves to allow a predetermined amount of air to enter the vacuum chamber to compensate for the reduced air volume presented when single breast pumping, so that the vacuum pressure applied to the breast remains relatively constant whether single or double-pumping.

As shown in FIGS. 7, 8, 20 and 21, passages 66a and 66c extend from passages 59a and 59c, respectively, to communicate with a respective port 42. (Two of the holes 64 which are depicted are non-functional in operation, but are part of the molding process.) The cylinder holder 32 includes a selector ring 70 for directing the vacuum to either or both of the ports 42 and then to breast pumps 22, as described in more detail hereafter.

Figure 3:
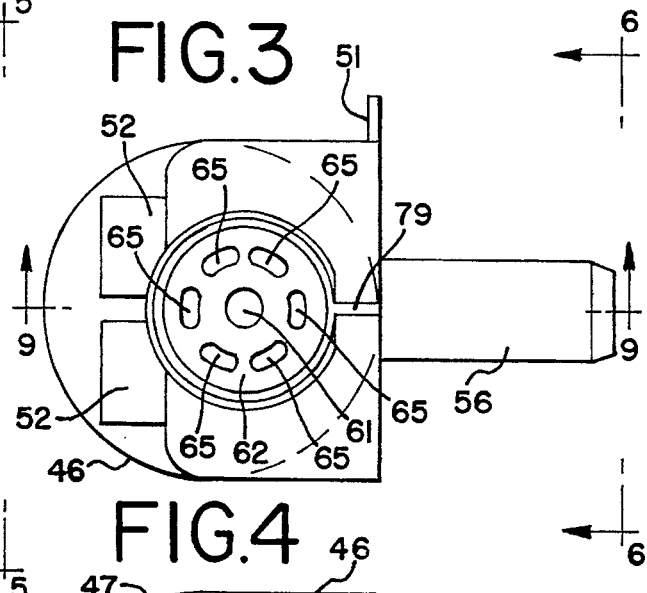
FIG. 3 is a front view of the cylinder holder taken along line 3—3 of FIG. 2, with a flap-valve removed for clarity.
Figures 3A, 3B:
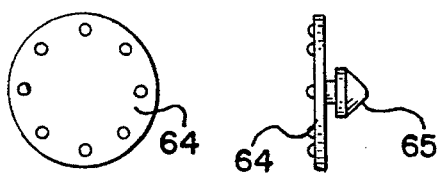
FIGS. 3A and 3B are a front and a side view of a flap valve.
Figure 4:
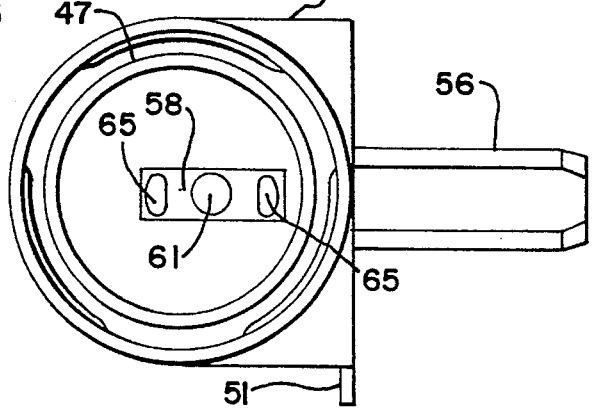
FIG. 4 is a rear view of the cylinder holder taken along line 4—4 of FIG. 2.
Figure 19:
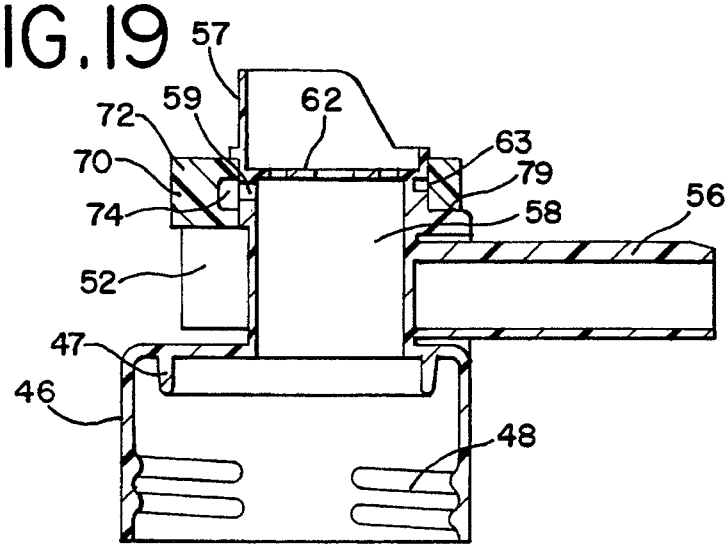
FIG. 19 is a view identical to that shown in FIG. 9, but with the addition of the selector ring in place.

With reference to FIG. 3, a flexible thin-disk 64 flap valve seal (FIGS. 3A and 3B) is positioned over a plurality of holes 64, 65 (and 66a, 66c) formed in the forward end portion 62 of the cylinder holder. A central post 67 formed integral with the flap valve 64 is received within hole 61 to secure the flap valve in place. When the piston rod 38 is pushed into the piston cylinder 36 on its return stroke, the air present in the chamber 58 is forced through the vacuum chamber 58 and the holes 65 (see FIG. 4) past the flap seal. On the other hand, when the piston rod 38 is pulled from the piston cylinder 36, the flap seal is pulled tight over the holes 65, 66a and 66c to create a seal. Consequently, a vacuum is formed in the chamber 58 on the pulling stroke. Such a flap valve and its operation are described in U.S. Pat. No. 4,929,229.

FIGS. 13–21 depict the selector ring 70 in detail. The selector ring includes an upraised indicator lever 72, an internal vacuum flow channel 74 and a plurality of small recessed channels 76. Referring to FIG. 2, the selector ring is received in a snug but rotatable fit around the collar 53, with the internal channel 74 overlying the holes 60a, 60b and 60c. The selector ring 70 is shown in place in FIGS. 19–21, for example. Markings (not depicted) provided on cowl 57 of the cylinder holder serve to orient the selector ring 70 in use. The middle marker corresponds to the "double breast pumping" setting for the breast pump assembly 20, and the side markers correspond, respectively, to the "single breast pumping" setting for either the left or the right breast pump 22 shown in FIG. 1. To select the desired breast pumping function of the breast pumping assembly 20, the indicator 72 of the selector 70 is rotated to the corresponding marker. A bead 49 is formed around the collar 53 to help keep the selector ring 70 in place on the collar 53.

Figure 20:
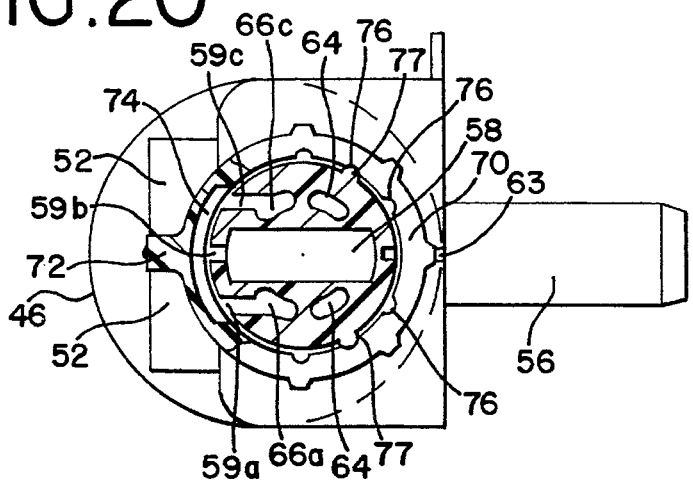
FIG. 20 is a view identical to that shown in FIG. 7, but with the addition of the selector ring, which is set to the double breast pumping position.

As best shown in FIG. 20, when the selector 70 is rotated on the collar 53 of cylinder holder 32 such that the indicator 72 is set to the "double pumping" marker, the vacuum flow channel 74 communicates with the passage 59b (which communicates with the vacuum chamber 58) and both of the passages 59a and 59c (which in turn are connected to the respective ports 42 via passages 66a and 66c). As can be understood, the vacuum generated in the piston cylinder 36 is drawn through the vacuum chamber 58 and through the passage 59b, which in turn draws vacuum through the channels 59a, 59c then through channels 66a, 66c to the ports 42. Thus, the vacuum is transmitted through the vacuum tubes 44 to the breast hoods 26 of each of the breast pumps 22. In addition, in the position shown in FIG. 20, the selector 70 blocks the leakage hole 63 in the double-pumping mode to prevent a reduction in vacuum pressure by air intake through hole 63.

Figure 21:
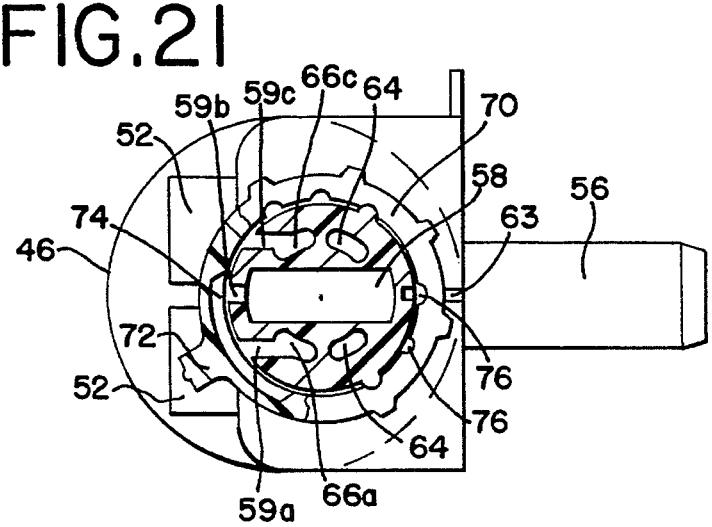
FIG. 21 is a view identical to that shown in FIG. 20, with the selector ring set to a single breast pumping position.
Figure 22:
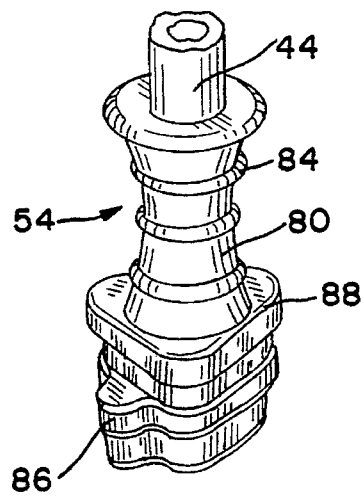
FIG. 22 is a perspective view of a male connector for connecting the tubing of a breast pump to the cylinder holder.
Figure 23:
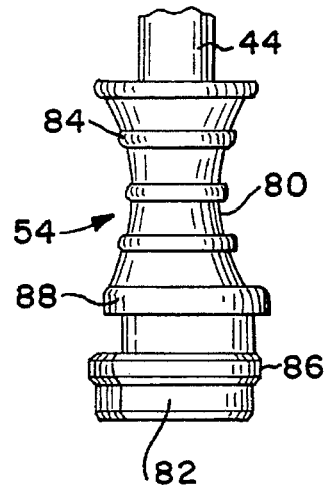
FIG. 23 is an elevational view of the male connector shown in FIG. 22.
Figure 24:
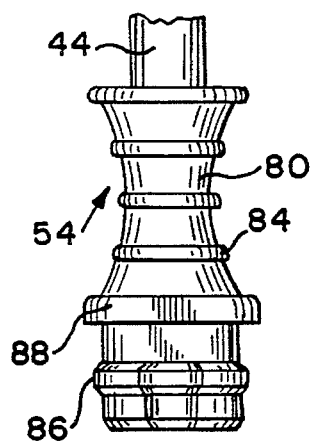
FIG. 24 is an elevational view looking at the left-hand side of FIG. 23.
Figure 25:
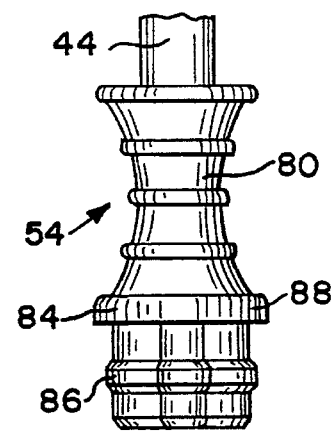
FIG. 25 is an elevational view looking at the right-hand side of FIG. 23.
Figure 27:
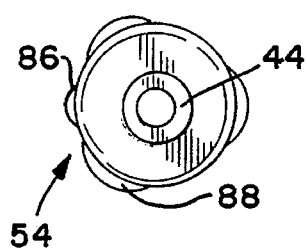
FIG. 27 is an end view of the top of the male connector shown in FIG. 23.
Figure 26:
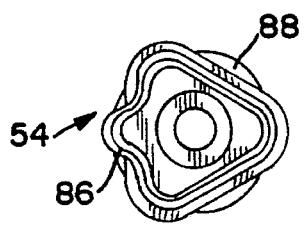
FIG. 26 is an end view of the bottom of the male connector shown in FIG. 23.

As shown in FIG. 21, when the selector 70 is rotated to a marker for "single breast pumping" (by either the left or right breast pump 22), the vacuum flow channel 74 communicates with only the vacuum chamber 58 via passage 59b and one of the passages 59a, 59c. In FIG. 21, the selector 70 covers the hole 60c, preventing a vacuum connection between the vacuum chamber 58 and the passages 59c, 66c. Thus, the vacuum is transmitted through only one port 42 and vacuum tube 44 to the respective breast pump 22 (in FIG. 21, via passages 59a, 66a).

Moreover, in the "single breast pumping" setting, one of the recess channels 76 formed in the selector 70 serves to uncover the leakage hole 63 to allow outside air to flow into the vacuum chamber 58, thereby reducing the vacuum pressure, in a predetermined manner, which otherwise would be generated by the piston pump 30. This is desirable to compensate for the reduced air volume in the system presented by only a single breast pump, so as to maintain substantially the same vacuum pressure to the breast pumps 22 whether one or both are being used. The recessed channels 76 also cooperate with elongated bosses 77 (FIGS. 5 and 6, for example) formed on the exterior of the collar 53 to position the selector ring 70 and hold it in place. A stop 79 is additionally provided to prevent over-rotation of the selector ring 70 when the stop hits recess 78 (see FIG. 15).

C. The Vacuum Connection

As shown in FIGS. 22–27, the vacuum tubes 44 terminate in male connectors 54, which are insertable into mating female receptacles 52 formed on the cylinder holder 32. This arrangement serves to provide an easily manipulated secure connection of the vacuum tubes 44 to the ports 42 on the cylinder holder 32.

The male connectors 54 include necked-in middle portion 80 and a port connector end 82. The middle portion 80 includes a number of ridges 84 for gripping the connector 54 and inserting or removing it into the corresponding female receptacle 52. Additionally, the male connectors 54 each include a sealing surface 86 for sealing the vacuum tubes 44 to the interior sidewalls of the receptacles 52. Moreover, a stop 88 is provided on each of the male connectors 54 to limit the engagement depth of the connectors 54 within the female receptacles 52.

D. Method of Breast Pumping

The present invention also provides an improved method for breast pumping that utilizes the above-described breast pump assembly 20. A woman desiring to express breastmilk removes the piston pump 30 from her manually-operated breast pump. The piston pump 30 is attached to an adapter, such as the aforedescribed cylinder holder 32, and mounted on a motor drive unit 24 that reciprocally moves the piston rod 38 within the piston cylinder 36 of the piston pump 30 to generate a vacuum. Two separate breast pumps 22 are attached, in a preferred embodiment, via separate vacuum tubes 44 to the piston pump 30. The cylinder holder is provided with a vacuum selector, such as selector ring 70, that allows the operator to quickly and easily select either or both of the breast pumps 22 for breast pumping, and to switch from one breast to the other. The woman then supports either or both of the breast pumps 22 on her breasts, depending on the mode of breast pumping that she desires, and activates the motor drive unit 24 for breast pumping. While it is conceivable that the foregoing method could be practiced without the use of the motor drive, i.e. manually, difficulties would be presented in maintaining the two breast pumps in place while also handling the piston pump.

It should be appreciated that the improved breast pump assembly 20 of the present invention may be modified or configured as appropriate for the desired application. The embodiment described above is to be considered in all respects only as illustrative and not restrictive. Changes may be made without departing from the spirit of the invention. All changes which come within the literal meaning as well as the range of equivalency of the claims are to be embraced within their scope.

What is claimed is:

1. An improved breast pump assembly comprising:

a piston pump having a piston which is reciprocated in a piston cylinder by a piston rod, a motor drive unit which reciprocally moves said piston rod within the interior of said piston cylinder to generate a vacuum, said piston cylinder further having an interior, an output end and another end through which said piston rod extends in use, a cylinder holder connected to said output end of said piston cylinder, said cylinder holder being mounted to said motor drive unit for reciprocal movement of said piston rod, said cylinder holder having two ports which communicate with said piston cylinder interior;

two breast pumping units each comprising a breast hood which receives a woman's breast therein for the expression of milk, a container for expressed milk which is in fluid communication with said breast hood, and a tube connected at one end to a respective one of said two ports and at the other end to a respective breast hood; and a selector on said cylinder holder, said selector being movable to connect a vacuum generated within said piston cylinder interior to one or both of said two ports.

2. The assembly of claim 1 wherein the selector is rotatably connected to the cylinder holder.

3. The assembly of claim 1 wherein the cylinder holder further comprises a non-circular cross-section female receptacle disposed around each of said two ports, and each said tube has a mating cross-section male connector at one end.

4. The assembly of claim 1 wherein the cylinder holder further comprises a leakage hole formed in said cylinder holder and extending between ambient atmosphere and a vacuum chamber formed within said cylinder holder, which vacuum chamber is in communication with said piston cylinder interior, said leakage hole allowing a predetermined amount of air into said cylinder holder to reduce the vacuum pressure generated within said vacuum chamber when only a single breast pumping unit is being used, the vacuum generated within a breast hood being essentially the same for a given piston stroke whether one or both of said breast pumping units are being used, and means for engaging and disengaging said leakage hole with ambient atmosphere.

5. The assembly of claim 4 wherein said leakage hole is disengaged by said selector when said selector connects the vacuum to both of said breast pumping units, and further wherein said leakage hole is engaged when said selector connects the vacuum to either one but not both of said breast pumping units.

6. A breast pump assembly for pumping a single breast as well as two breasts simultaneously, comprising:

a source of intermittent vacuum, two breast pumping units each comprising a breast hood which is adapted to receive a woman's breast therein for the expression of milk, a container for expressed milk which is in fluid communication with said breast hood, and a tube connected at one end to a respective breast hood; and a connector device for selectively connecting said vacuum source to said breast pumping units with intermittent vacuum thereby being selectively generated in each said breast hood to effect the expression of milk from a breast, said connector device having an internal chamber in communication with said vacuum source and a pair of ports in communication with said internal chamber, each said port receiving another end of a respective tube therein to place said breast hood in communication with said vacuum source, and a selector on said connector device, said selector connecting and disconnecting either port as well as both ports simultaneously to said internal chamber to effect single and double pumping.

7. The assembly of claim 6 wherein said source of intermittent vacuum is a piston pump having a piston which is reciprocated in a piston cylinder by a piston rod, said piston cylinder further having an interior and an output end, and said connector device is in the form of a cylinder holder which is received on said output end of said piston cylinder, said piston pump being used to generate said intermittent vacuum through reciprocation of a piston rod within the interior of said piston cylinder to generate a vacuum, said piston cylinder further having another end through which said piston rod extends in use.

8. The assembly of claim 7 further including a motor drive unit for reciprocally moving said piston rod within said piston cylinder to generate a vacuum, said cylinder holder in use being mounted on said motor drive, said motor drive having means to reciprocate said piston rod within said piston cylinder.

9. The assembly of claim 8 wherein said selector is rotatably carried on said cylinder holder.

10. The assembly of claim 9 wherein said cylinder holder further comprises a leakage hole formed in said cylinder holder and extending between ambient atmosphere and a vacuum chamber formed within said cylinder holder, which vacuum chamber is in communication with said piston cylinder interior, said leakage hole reducing the vacuum pressure generated within said vacuum chamber when only a single breast pumping unit is being used, the vacuum generated within a breast hood being essentially the same for a given piston stroke whether one or both of said breast pumping units are being used, and means for engaging and disengaging said leakage hole with ambient atmosphere.

11. The assembly of claim 10 wherein said leakage hole is disengaged by said selector when said selector connects the vacuum to both of said breast pumping units, and further wherein said leakage hole is engaged when said selector connects the vacuum to either one but not both of said breast pumping units.

12. The breast pump assembly of claim 6 wherein said selector is rotatably mounted on said connector device, and said connector device has a first hole extending therethrough which is in communication with one of said ports, a second hole extending therethrough which is in communication with the other of said ports, and a third hole extending therethrough which is in communication with said internal pathway, said selector having a base with a cavity formed therein, said base having a substantially airtight engagement with said connector device in the vicinity of said cavity such that said cavity forms an air channel which overlies said three holes in a first position to place both said first and second holes in communication with said vacuum source via said third hole, said selector when rotated from said first position selectively covering one of said first and second holes in a second position such that only the other of said first and second holes is placed in communication with said vacuum source.

13. The breast pump assembly of claim 12 wherein said connector device further comprises a leakage hole formed in said connector device and extending between ambient atmosphere and said vacuum chamber, said leakage hole reducing the vacuum pressure generated within said vacuum chamber when only a single breast pumping unit is being used, the vacuum generated within a breast hood being essentially the same for a given piston stroke whether one or both of said breast pumping units are used, and wherein said selector selectively covers and uncovers said leakage hole when said selector is rotated to engage and disengage said leakage hole with ambient atmosphere.

14. A method for pumping a single breast as well as two breasts simultaneously, comprising the steps of:

providing a source of intermittent vacuum, providing two breast pumping units each comprising a breast hood which receives a woman's breast therein for the expression of milk, a container for expressed milk which is in fluid communication with said breast hood, and a tube connected at one end to a respective breast hood;

providing a connector device for selectively connecting said vacuum source to said breast pumping units with intermittent vacuum being generated in each said breast hood to effect the expression of milk from a breast, said connector device having an internal chamber in communication with said vacuum source and a pair of ports in communication with said internal chamber, each said port receiving another end of a respective tube therein to place said breast hood in communication with said vacuum source, and a selector on said connector device, and operating said selector to connect and disconnect either port as well as connecting both ports simultaneously to said internal chamber to effect single and double pumping.

* * * * *